United States Patent [19]
Rosen

[11] Patent Number: 5,014,041
[45] Date of Patent: May 7, 1991

[54] SHOE FITTING SYSTEM

[76] Inventor: Henri E. Rosen, 229 Coolidge Ave., Watertown, Mass. 02172

[21] Appl. No.: 505,931

[22] Filed: Apr. 6, 1990

Related U.S. Application Data

[63] Continuation of Ser. No. 348,261, May 5, 1989, Pat. No. 4,931,773.

[51] Int. Cl.⁵ .............................................. G08B 21/00
[52] U.S. Cl. ..................... 340/573; 36/25 R; 36/43; 36/112; 36/139; 116/67 R; 340/540
[58] Field of Search ............. 340/573, 540; 116/67 R, 116/200; 36/112, 139, 43, 44, 25 R, 11.5, 98, 103

[56] References Cited

U.S. PATENT DOCUMENTS

| | | | |
|---|---|---|---|
| 621,892 | 3/1899 | Azzimonti | 116/67 R |
| 2,109,780 | 3/1938 | Mott | 36/1 |
| 2,126,608 | 8/1938 | Brady | 36/1 |
| 2,255,099 | 9/1941 | Brady | 36/1 |
| 2,303,431 | 12/1942 | Brophy | 36/25 R |
| 2,464,571 | 3/1949 | Gardner | 36/1 |
| 3,702,999 | 11/1972 | Gradisar | 340/573 |
| 3,974,491 | 8/1976 | Sipe | 340/573 |
| 4,253,254 | 3/1981 | Gill | 36/139 |
| 4,646,350 | 2/1987 | Batra | 340/540 |
| 4,787,100 | 11/1988 | Jonat | 36/112 |

Primary Examiner—Glen R. Swann, III
Attorney, Agent, or Firm—Bruce F. Jacobs

[57] ABSTRACT

A system for better determining the fit of shoes, particularly children's shoes, is described wherein transparent areas are provided in the shoe bottom along with fitting indices to enable comparison of the outline of a foot in the shoe to the fitting indices. The shoe may also be provided with optional audio-visual warning means to signal when the shoe is about to be outgrown.

4 Claims, 5 Drawing Sheets

SHOE FITTING SYSTEM

This is a continuation of copending application Ser. No. 07/348,261 filed on May 5, 1989, now U.S. Pat. No. 4,931,773, issued June 5, 1990.

This invention relates to a system for fitting shoes, and more particularly for fitting children's shoes. It has long been known that serious damage can be done to the feet of growing children, should the children continue to wear shoes that they have outgrown or that otherwise fit improperly.

The principal problems in obtaining and maintaining proper fit in children's shoes stem from the difficulty of knowing the exact position of the outside perimeter of the toes and the ball area of the foot when it is actually in the shoe, as opposed to where these parts of the foot should be, from the time of purchase to the time at which the child's foot is about to outgrow the shoe. Wearing the shoe beyond the time when the child's foot outgrows the shoe may put a child's foot health in jeopardy.

Prior attempts to address these problems largely focused on approaches involving the old radiographic or x-ray fitting devices that display the flesh and bones of the forepart of the foot in the shoe, on a fluorescent screen. These were popularly used in shoe stores in the 1930's and 1940's, until the damaging potential of radiation was better understood at which point the use of such invasive equipment was effectively terminated. Such approaches are disclosed, for example, in U.S. Pat. Nos. 2,109,780, 2,126,608 and 2,255,099.

Other prior attempts at devising a shoe fitting system, include the non-invasive foot or sock marking insole described in U.S. Pat. No. 2,464,571. This never became popular, probably because this approach seems to have been imprecise, prone to errors, and a bother to use, especially in comparison to the conventional manual pressure approach, which arrives at similarly imprecise conclusions.

Alarm and sound systems in shoes are not new, as can be seen in U.S. Pat. Nos. 3,702,999 and 4,646,350, but their use to indicate shoe fit or non-fit, as described in this invention, is novel.

What is needed and is provided by the present invention is a non-invasive fitting system built into every shoe irrespective of the design of its upper and easily usable to determine the correct size at time of purchase and also to indicate the proper time for replacement by a larger size. An optional but preferred audible alarm helps ensure monitoring of proper fit by parents or teachers to better avoid the dangers inherent in impaired foot growth that may be caused by the wearing of shoes that are too short or snug for the child's foot.

Among the objects of this invention is the provision of a shoe fitting system that is simple and accurate to use and that will allow easy determination of the position and fit of a shoe on a foot throughout the useful life of said shoe.

Other objects of the invention include means to determine the correct size shoe for a child at the time of purchase, with further means to monitor the growth of the foot in the shoe to the point where the shoe is about to be outgrown and should be replaced by one of larger size.

A further object of the invention is to provide optional means to signal when a shoe is about to be outgrown.

Another object of the invention is to provide optional means whereby a shod foot can be viewed in both weightbearing and non-weightbearing conditions.

For a fuller understanding of the nature and objects of the present invention, reference should be made to the following detailed description taken in connection with the accompanying drawings.

DETAILED DESCRIPTION OF THE INVENTION

Figure 1:
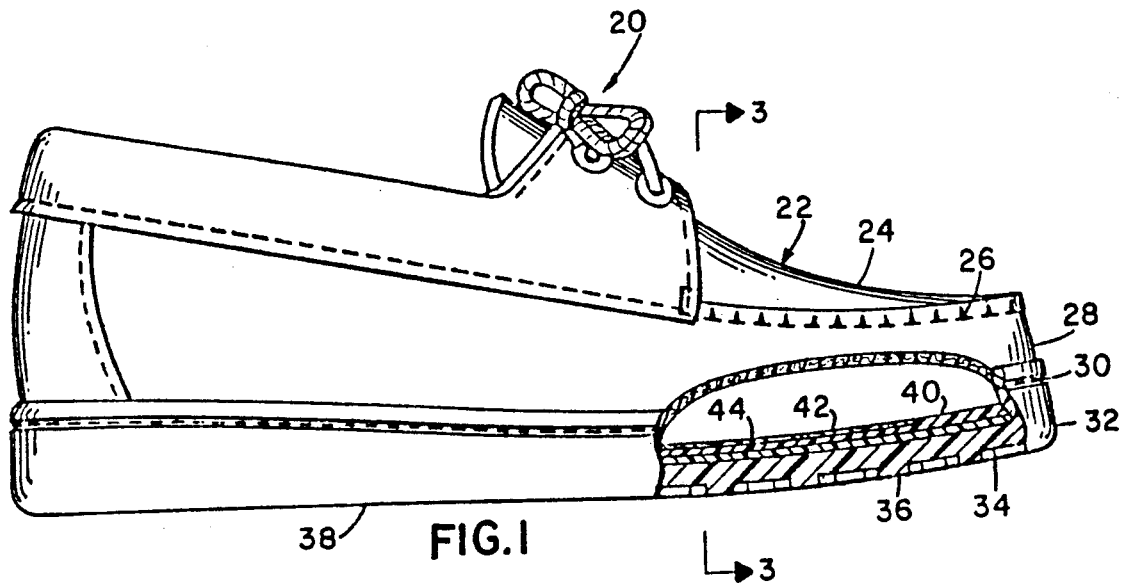
FIG. 1 is a side elevational partially cutaway view of a shoe embodying principles of the present invention.

Referring to the drawings, the shoe fitting system of the present invention will be described with reference to a children's moccasin styled boat shoe, with a unitsole having upstanding sidewalls, and often referred to as a cup or sidewall unitsole. It should be understood that this is being done for ease of reference, and that this invention is applicable as well to other constructions, particularly stitchdowns, to other size ranges, and to a wide range of styling of both upper and bottom elements.

Figure 2:
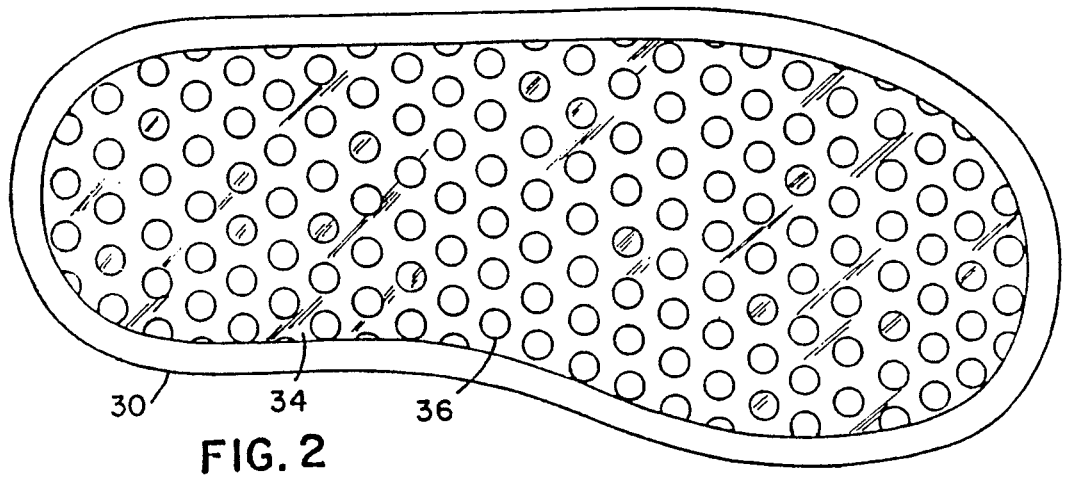
FIG. 2 is a plan view of the bottom of the unitsole of the shoe of FIG. 1.
Figure 3:
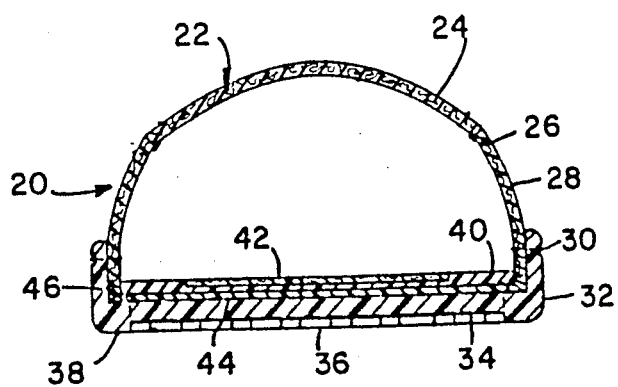
FIG. 3 is a transverse cross-sectional elevation of the shoe of FIG. 1 taken along ball line 3—3 thereof.

Referring to the drawings, FIGS. 1-3 show a shoe 20 comprising an upper 22 including a plug 24 fastened preferably by stitching 26 to vamp 28. The upper 22 is also connected, preferably by stitching, to a transparent socklining 44, preferably composed of a clear vinyl material, and to unitsole 32 by a suitable means, such as stitching 30 and 46 and/or adhesive cement (not shown). Unitsole 32 preferably comprises two members, outer wall member 38 and central panel 34, and is preferably molded to form a unitary structure. The outer upstanding wall 38 is nontransparent and preferably colored to harmonize with the color and design of upper 22. Central panel 34 is made of clear polymeric, i.e. vinyl or polyurethane, materials having a plurality of non-lighttransmissable lugs 36 which act as the wearing surfaces and also serve to minimize abrasion, and thus retain the transparency, of the clear recessed areas therebetween. The shoe also contains a transparent insole insert 40, preferably made of a substantially clear vinyl or polyurethane material, and a sock 42 heat-sealed flush therewith. Sock 42 may be made of Cambrelle ® fabric, available from Faytex of Braintree, Mass., or any other suitable sock material. Alternatively, insert 40 may be opaque, and made from a material such as Texon ® sheet insole material of Texon, Inc. of Westfield, Mass. which is designed for removal and reinsertion into a shoe. Suitable materials preferably have a flat surface but may have irregularities or protuberances thereon as is known in the art; for example, as possessed by 'Noppy Trim' sandals from Birkenstock of Novato, Calif. While such surface protuberances will usually be placed on the insole or socklining surfaces which will contact the foot, they could also be molded integral with a unitsole or on the top surfaces of a molded sole or midsole units.

Figure 4:
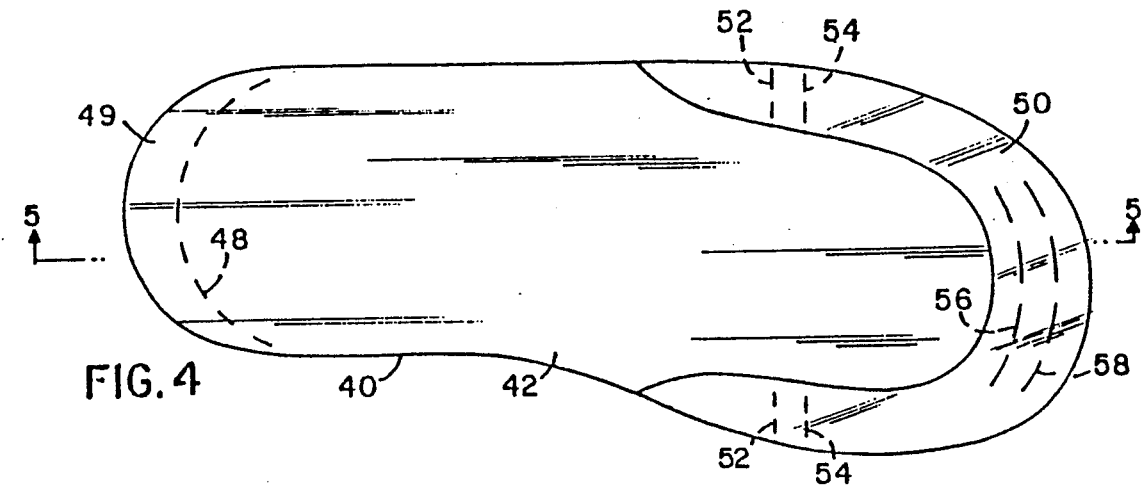
FIG. 4 is a plan view of the insole of the shoe of FIG. 1.
Figure 5:
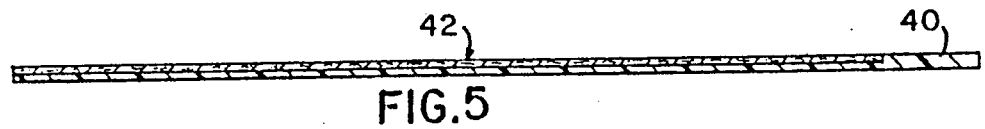
FIG. 5 is a side sectional cross-section of the insole of FIG. 4, taken along the longitudinal centerline thereof.

FIG. 4 is a plan view of the insole of FIG. 1, showing a transparent insole 40 partially covered by opaque sock 42, which can optionally be shortened at the heel, as shown by the dashed line in FIG. 4, to allow the position of the heel in the shoe to be viewed through optional transparent window 49 formed by the positions of members 40, 42, and 44. The clear forward areas 50 of insole 40 include reference markings at ball 52, 54 and toe 56, 58 regions, which may optionally be printed or molded into socklining 40 or, alternatively, unitsole 32, and which would preferably also include imprinted designations for visual comparisons of a foot thereon, with markings 52 and 54 showing the location of the ball of the child's foot at purchase and at the relative end of the shoe's fitting life on that foot respectively. Markings 56 and 58 similarly show the recommended locations of the ends of the toes both at purchase and at the end of the recommended fitting life of the shoe. Optional heel window 49 can be used to ensure that the foot is well back in the shoe when visual checks of fit reference markings 52, 54, 56 and 58 are made. The foot can be visually observed in a non-weightbearing attitude simply by raising the shod foot and checking its position in the shoe as described above. Alternatively, the visual check could be made while foot and shoe are in a weight-bearing attitude by having the child stand on a supported clear panel, having illumination means and an angled mirror thereunder to allow easy viewing of the weightbearing relationships of foot position to shoe reference points. FIG. 5 shows a longitudinal side elevation of the insole of FIG. 4. In the event an opaque re-insertable insole is used, it would have to be removed from the shoe to allow inspection of the foot position in the shoe.

Figure 6:
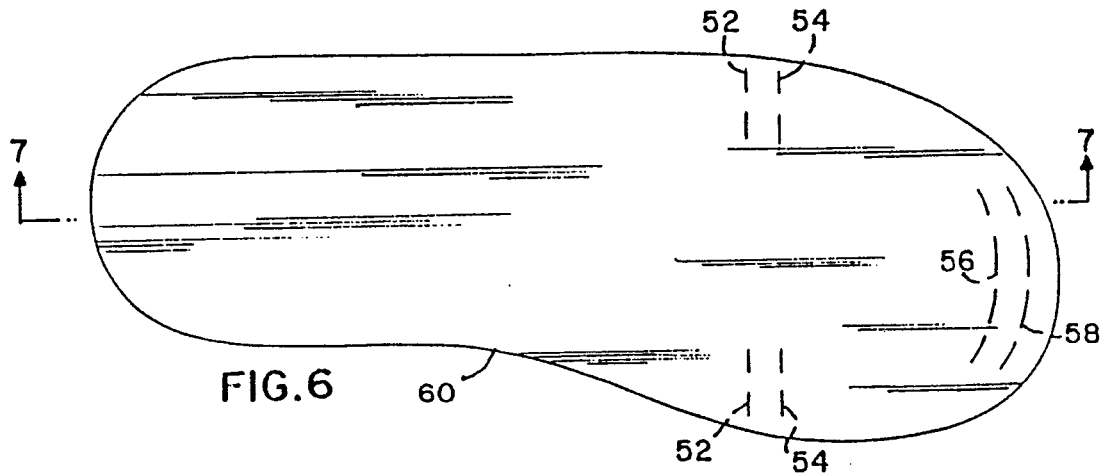
FIG. 6 is a plan view of a first alternative insole that could be optionally used in place of the insole shown in FIG. 1.

FIG. 6 shows another embodiment of the invention comprising an additional removable insole insert 60, having fit reference markings 52-58 thereon, similar to those on insole 40 in FIG. 4. In this embodiment there is no requirement for members 40 and 44 being transparent.

Figure 7:
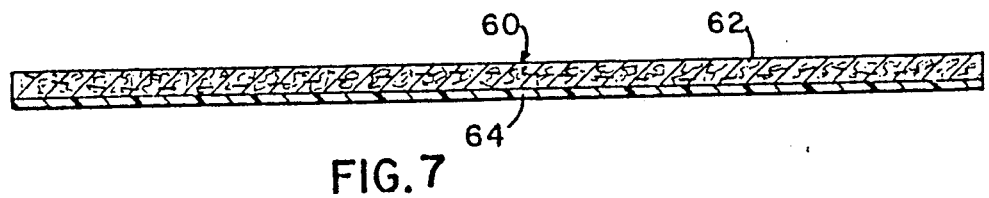
FIG. 7 is a side section of the insole of FIG. 6, taken along the centerline thereof.

FIG. 7 shows the insole of FIG. 6 in a side elevational cross-sectional view, wherein the insole 60 comprises top surface member 62, preferably comprised of a slow recovery plastic foam similar to T-Foam ®, a porous open-cell polyether-based polyurethane foam available from AliMed of Dedham, Mass. Supporting the surface element 62 and attached thereto preferably by adhesive means is a supporting insole member 64, preferably made of Texon ® insole material or other similar insole material. So constructed, insole insert 60 when removed after weight-bearing use will temporarily show an actual imprint of the foot under weightbearing, i.e. standing and/or walking, conditions. The foam can be compounded to have a slow enough recovery rate so that the impression of the foot thereon will remain long enough to make a visual check against markings 52-58.

Alternatively an encapsulated preferably translucent 'flow' material such as has been used inside plastic ski boot shells may be used as an insert together with the clear vinyl insole of FIG. 4. Examples of such materials include phenolic resin beads embedded in silicone lubricating grease, small pieces of cork suspended in petroleum and other fluids including a variety of liquids and air. The foot position would be viewed as in the embodiment of FIG. 7, with the added benefits of the viewable impression temporarily retained by the gel. Another alternative utilizes temporarily markable insoles, which may be made of laminates similar to those used on the so-called "magic slate" used by children, wherein a clear plastic cover panel adheres to a plastic underlayer when under the pressure of a pointed stylus, leaving a visible mark which disappears as the clear cover panel is peeled away from said underlayer.

Figure 8:
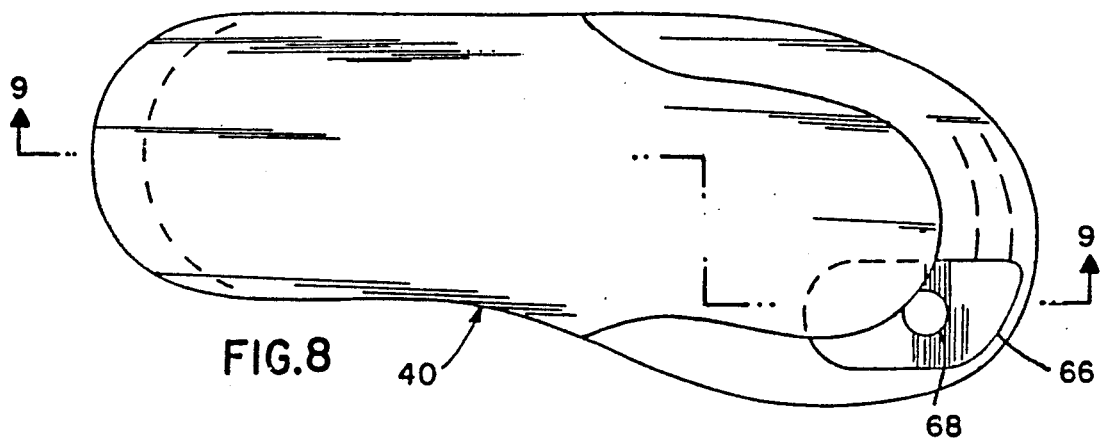
FIG. 8 is a plan view of a second alternative insole.

Another embodiment is shown in FIG. 8 wherein the insole of FIG. 4 is shown with an optional metal "cricket" spring (activated) noisemaker 66 such as that available from the M. Pressner Co., Inc. of Brooklyn, N.Y. inserted therein. The noisemaker is designed to click as indented area 68 deforms when pressure of a wearer's big toe depresses the insole 40 and the spring 66 to the flat position 70 from its normal at rest upwardly curved position as drawn. The clicker spring 66 is positioned to operate only at such time as the child is about to outgrow the shoe, i.e. when the big toe is positioned far enough forward in the shoe to depress the insole 40 as well as the clicker spring 66 contained therein. Alternately, such a spring could be positioned in the insole or sole assembly far enough forward of the ball line at purchase, so that it would deform and sound its typical clicking sound, when the ball of the foot and its hingeing action had grown forward in the shoe to the point that the shoe was starting to be outgrown, and in need of replacement by one of a suitably larger size.

Figure 9:
FIG. 9 is a side section of the insole of FIG. 8 taken along line 9—9 thereof.

FIG. 9 shows the upwardly curved end of insole 40 with a spring 66 installed therein. Optionally, but not shown, a second louder spring could be installed beside spring 66 and a bit forward thereof to sound a louder and more insistent alarm as the foot growth continues, to enable timely replacement of the shoe by one of a suitably larger size before the foot sustains damage. Alternatively, such spring(s) could be built into unitsole 32, or inserted between socklining 44 and unitsole 32, but the preferred embodiment is as shown in FIGS. 8 and 9 since the clicker spring could be made more easily removable, should the parent so prefer.

Figure 10:
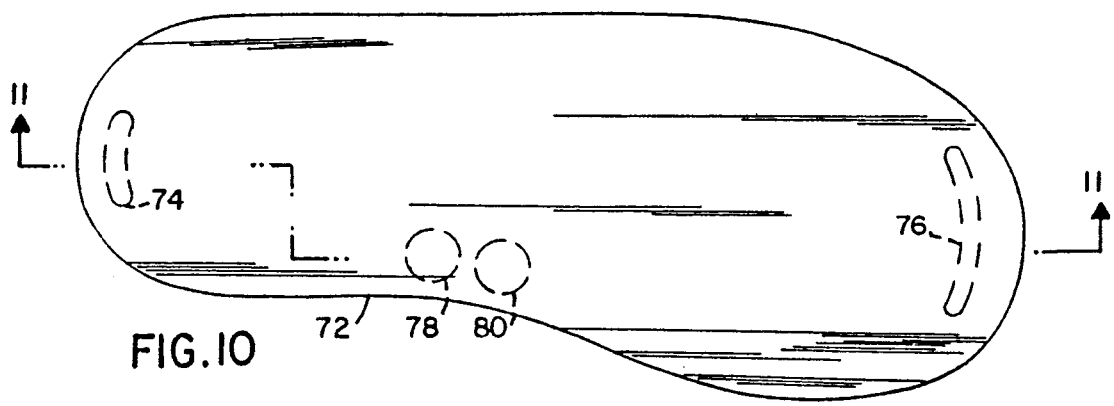
FIG. 10 is a plan view of a third alternative insole.

FIG. 10 shows another embodiment of the invention, wherein insole insert 72 is provided with electrical membrane keypad switches 74 and 76 such as manufactured by Techprint, Inc. of Woburn, Mass., a battery 78, and electronic circuitry incorporating use of a sound chip 80 to provide an audible response.

Additional circuitry and elements, including solar panels and other audio and/or visual signals and displays could optionally be included in either the upper or sole, along with connecting means for such to the insole circuitry.

Figure 11:
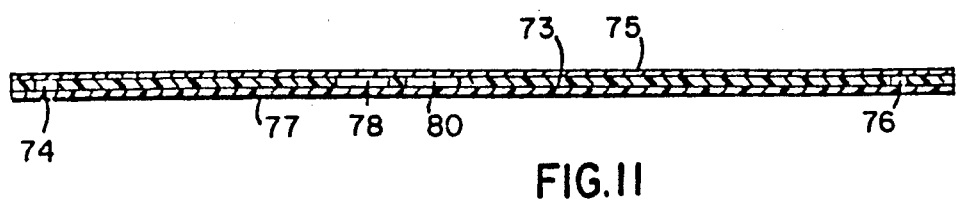
FIG. 11 is a side section of the insole of FIG. 10.

FIG. 11 shows a longitudinal side elevational cross section of the insole of FIG. 10, wherein a resiliently compressible foam layer 73 is bonded between a resiliently flexible top layer 75 and bottom supporting layer 77. Top layer 76 is made of Cambrelle ® fabric or a similar material, coated on the underside to allow the printing thereon of a printed circuit, connecting pressure switches 74 and 76 at heel and toe, respectively, to a battery 78 and signal generator and speaker assembly 80. The purpose and function of the two switches is to insure that the child's heel is well back in the shoe so that the alarm that sounds as the growing toes reach the danger will not be set off falsely, should the child's foot slip or slide forward in, for example, an untied, or too loosely-laced, shoe. Optional variations, but not shown include additional and similarly acting twin pressure switches on the insole at both sides of the ball area thereof, to monitor width growth of the foot in the shoe along with the length growth monitoring described. Other suitable options include flashing light sources for use instead of or, in addition to, the audible alarm, as well as audio and/or visual means to advise not only when the next size is needed, but with recommendations as to exactly what that size should be.

Figure 12:
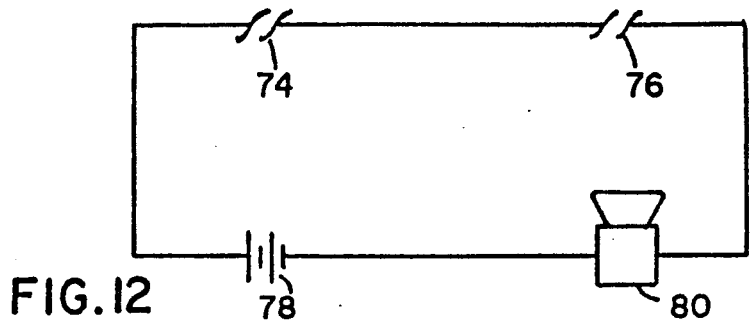
FIG. 12 is a schematic circuit diagram showing the electrical and electronic elements included in the insole of FIGS. 10 and II.

FIG. 12 shows a simplified circuit diagram for the electrical and electronic elements used in the insole of FIGS. 10-11, comprising switches 74 and 76, battery 78 and sound generator/audio electronic signal source assembly 80. Switches 74 and 76 are similar to these used in pocket calculators such as Casio ® S1-760 and the battery is similar to those used in solid state electronic wrist-watches. Alternatively, the power source may be one or more light-activated solar panels, on an outer surface of the shoe, electrically connected to the sensing and signaling circuitry of the sole.

In the embodiments of FIGS. 8-12, members such as 34, 40 and 44 need not be transparent.

Figure 13:
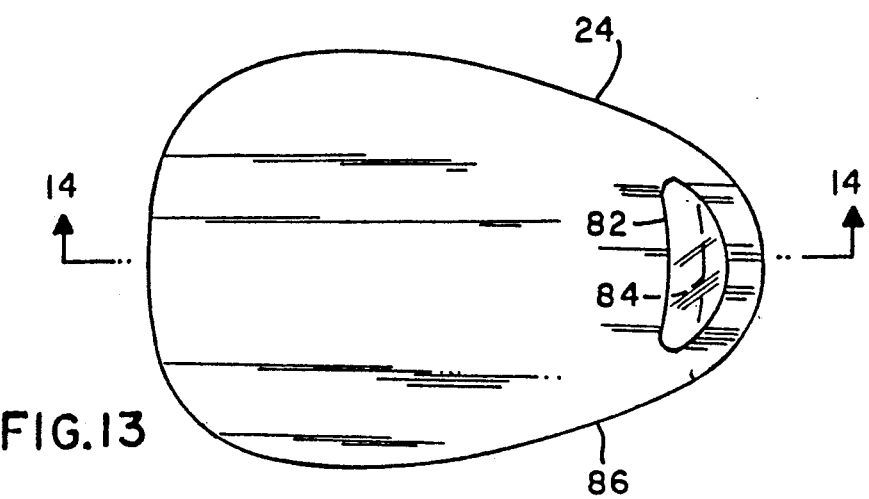
FIG. 13 is a plan view of an optional "windowed" plug, for alternative use in place of the plug drawn in FIG. 1.

FIG. 13 shows still another embodiment of the invention in which plug 24 is provided with at least one transparent window 82, through which the ends of the toes of a foot in the shoe can be viewed both when the foot and shoe are weightbearing and non-weightbearing. Such window or windows can be provided with reference marking 84, to determine, for example, when the foot is in the safe fitting area in the shoe. The perimeter of such window or opening could be designed to provide the same function. Similar windows or openings (not shown) at each side of the ball could allow additional viewing of the ball position as well as the relative fit of the foot's width to that of the shoe thereon.

Figure 14:
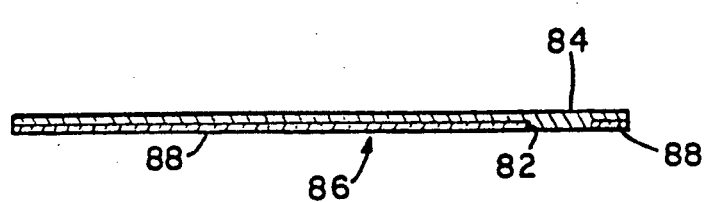
FIG. 14 is a longitudinal cross-section of the plug of FIG. 13 taken along the centerline thereof.

FIG. 14 shows plug 24 as a laminate, with the outer surface 86 of clear transparent vinyl or polyurethane material, with a windowed opaque lining 88, heat-sealed or molded flush therewith. Lining 88 is preferably made of Cambrelle ® fabric, but could also be made of any other material suitable for wearing next to the foot, including thin leather.

Figure 15:
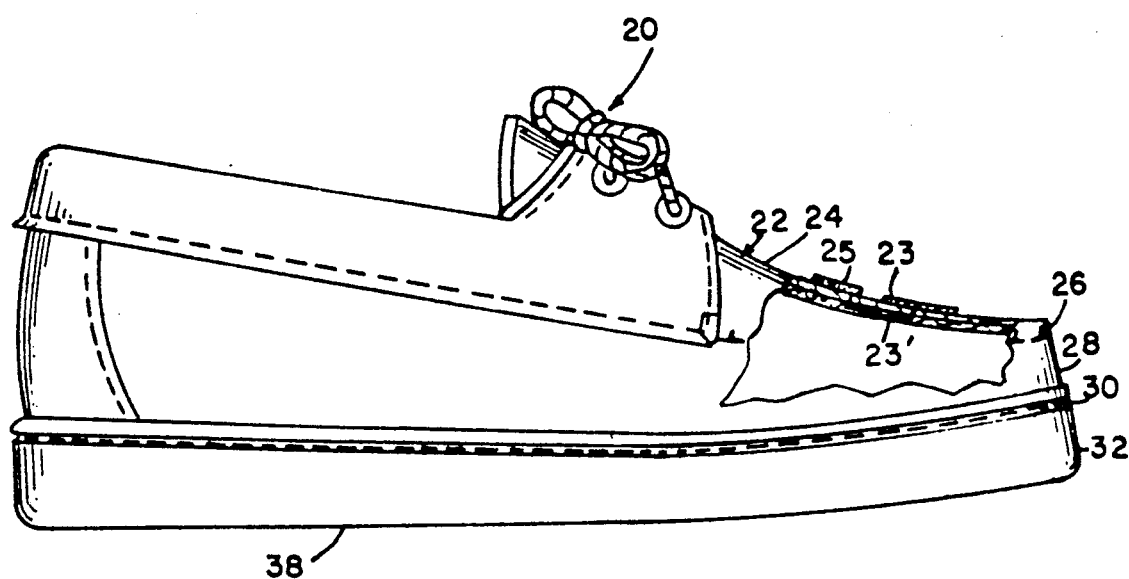
FIG. 15 is a side elevation partially cutaway view of a shoe embodying principles of the present invention.

FIG. 15 shows still another embodiment of the invention in which as in FIG. 1 a shoe 20 comprises upper 22 including plug 24 fastened by stitching 25 to unitsole 32 by stitching 30. In this embodiment, a light-activated solar panel 23 is attached to plug 24 and is used to power visual display 26 (also attached to plug 24) to which it is electrically connected by wire 23'.

I claim:

1. A shoe fitting system comprising shoe containing therein a light producing means for generating a visual signal when a foot inserted in the shoe begins to outgrow the shoe.

2. The shoe fitting system of claim 1, wherein the light producing means comprises a circuit having at least one switch, a power source means, and a light generating means.

3. The shoe fitting system of claim 1, wherein the power source means is a battery.

4. The shoe fitting system of claim 1, wherein the power source means is a solar panel.

* * * * *